United States Patent [19]
Fahmy

[11] Patent Number: 5,456,971
[45] Date of Patent: Oct. 10, 1995

[54] COVERING WEB HAVING DISCRETE REGIONS POSSESSING DIFFERENT DRAINAGE CAPABILITIES

[75] Inventor: Tarek Fahmy, Peine, Germany

[73] Assignee: Corovin GmbH, Peine, Germany

[21] Appl. No.: 70,448

[22] PCT Filed: Dec. 7, 1991

[86] PCT No.: PCT/DE91/00962

§ 371 Date: Jul. 30, 1993

§ 102(e) Date: Jul. 30, 1993

[87] PCT Pub. No.: WO92/12281

PCT Pub. Date: Jul. 23, 1992

[30] Foreign Application Priority Data

Dec. 27, 1990 [DE] Germany ............................ 40 41 999.1
Mar. 19, 1991 [DE] Germany ............................ 41 08 937.5

[51] Int. Cl.⁶ .................................................. D04H 1/04
[52] U.S. Cl. .................... 428/212; 428/114; 428/171; 428/286; 428/299; 428/301; 428/298; 428/296; 428/297; 428/903; 428/288; 604/358; 604/366; 604/370; 604/385.1
[58] Field of Search ........................ 428/114, 171, 428/286, 299, 301, 298, 296, 297, 903, 288, 212; 604/358, 366, 370, 385.1

[56] References Cited

U.S. PATENT DOCUMENTS

| | | | |
|---|---|---|---|
| 3,768,118 | 10/1973 | Ruffo et al. ............................ | 264/511 |
| 3,949,130 | 4/1976 | Sabee et al. ............................ | 428/192 |
| 4,041,203 | 8/1977 | Brock et al. ............................ | 428/157 |
| 4,661,390 | 4/1987 | Kelchner, Jr. ............................ | 428/113 |
| 4,714,647 | 12/1987 | Shipp, Jr. et al. ............................ | 428/212 |
| 4,725,473 | 2/1988 | Van Gompel et al. ............................ | 428/156 |
| 4,751,134 | 6/1988 | Chenoweth et al. ............................ | 428/284 |
| 4,762,520 | 8/1988 | Wallström ............................ | 604/366 |
| 4,767,586 | 8/1988 | Radwanski et al. ............................ | 264/113 |
| 4,910,064 | 3/1990 | Sabee ............................ | 428/113 |
| 4,950,531 | 8/1990 | Radwanski ............................ | 428/284 |
| 5,145,727 | 9/1992 | Potts et al. ............................ | 428/198 |

Primary Examiner—George F. Lesmes
Assistant Examiner—Kathleen L. Choi
Attorney, Agent, or Firm—Burns, Doane, Swecker & Mathis

[57] ABSTRACT

A coveting web formed by a compound web material of coarse filaments and fine microfibers constituting a mixture without discrete phase boundaries between the individual components. The compound web material is produced in an integrated formation process on the same layering device of a web-forming installation. As a novel feature, the compound web material has strip-like regions not forming a mixture but consisting only of coarse filaments or containing only a small proportion of free microfibers. These strips are bordered on either side by other strips containing a mixture of both components—coarse filaments and free microfibers.

5 Claims, 3 Drawing Sheets

FIG. 5
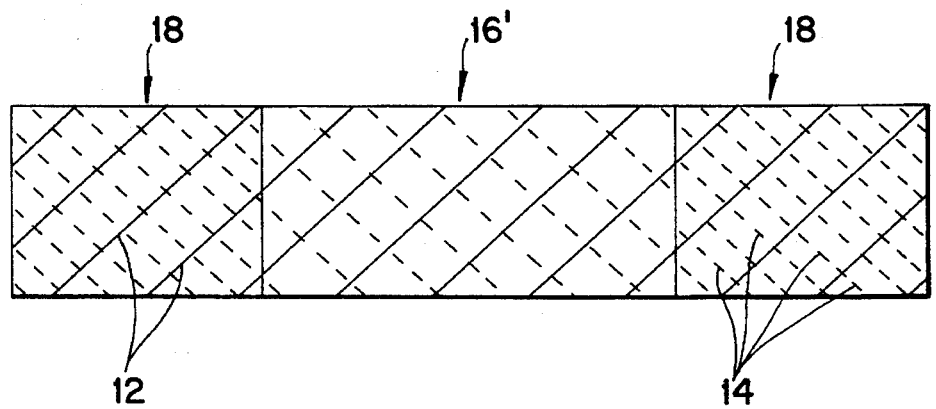
FIG. 6
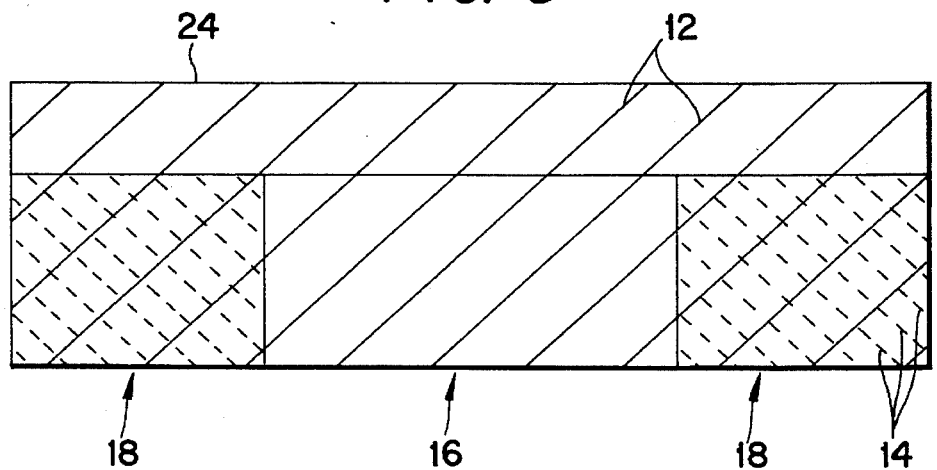
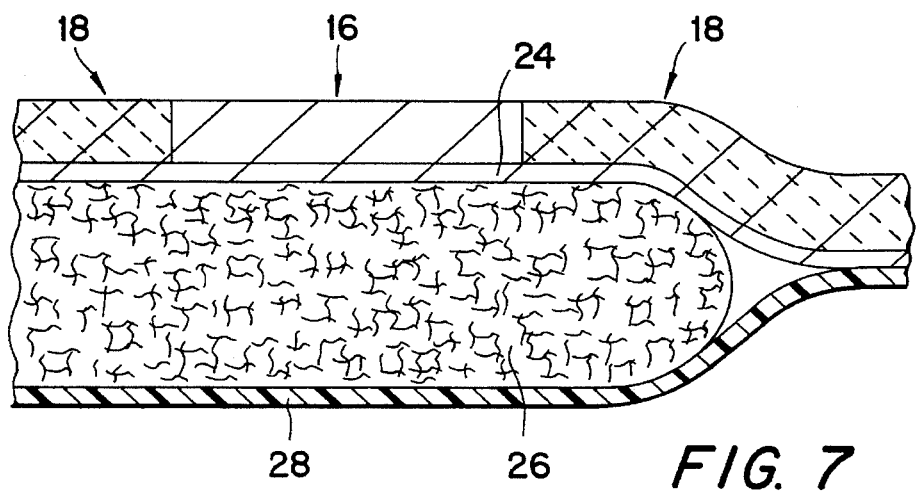
FIG. 7

COVERING WEB HAVING DISCRETE REGIONS POSSESSING DIFFERENT DRAINAGE CAPABILITIES

The invention relates to a covering web, suitable for use in the production of absorptive products such as diapers and sanitary napkins.

BACKGROUND OF THE INVENTION

In German Patent Application P 39 20 066.3 a compound web material, which can be applied as a covering web, is described; said compound web material is characterized by a mixture of coarse filaments and free microfibers without the presence of discrete layers with a phase boundary between the individual components. Rather the compound web material is formed on a layering device by simultaneously depositing with blowing both components, so that the compound web material consists of a mixture of coarse filaments and fine microfibers and thus represents an integrated material.

An important advantage of this compound web material lies in the fact that due to the formed mixture of different components there is no gradient over the cross section with respect to the different diameters of the fibers. Nevertheless, both functions peculiar to the different fiber components are combined. These respective functions extend over the entire cross section of the compound web material.

Since, when viewed over the entire cross section, the individual components are mixed together, the components can also exert the functions assigned to them over the entire cross section, a feature that is not possible with known layered materials with discrete phase boundaries. A conceivable function with respect to the free microfibers is the filtration or the transport of liquids. Due to the distribution of the microfibers over the layer thickness of the compound web material, a higher rate of filtration can be obtained, with the distribution being achieved as a consequence of thorough mixing.

Thus, the aforementioned German Patent Application describes in total an improved compound web material, which exhibits higher efficiency with respect to the functions intrinsic to the individual components. Thus, significantly improved applications are opened to the compound web material.

Nevertheless, there are still fields of application in which even said compound web material cannot be optimally used. Therefore, the invention is based on the problem of designing said compound web material in such a manner that the field of application is even more expanded and more efficient, in particular when using the compound web material as a covering material for the absorptive body of absorbent products, such as diapers, sanitary napkins or the like.

SUMMARY OF THE INVENTION

The fundamental idea of the invention consists of designing the compound web material in such a manner that it exhibits different regions, which correspond to the respective requirements and in which the mixing ratios of the two components (coarse filaments and fine microfibers) are different. Thus, separate regions of compound web material can be realized, and said regions can assume different functions.

In the case of diapers, for example, such a web material has an important advantage, when the compound web material or covering web is used for the absorptive body of the diaper. Owing to the different mixing ratios different regions of the diaper surface can be realized, said regions being desired with respect to the permeability to moisture or the moisture-repelling function.

At the same time, it is possible to provide for hydrophilicity only in the central section of the covering layer of the diaper and thus to design here the actual drainage region (i.e., an area having an increased drainage capability). The two side strips can be designed so as to be hydrophobic in an advantageous manner.

In the invention it is provided, e.g., that the compound web material comprises only partially two components so that one or more discrete regions are provided that are formed exclusively by the coarse filaments. In this embodiment there are, thus, discrete regions exhibiting no mixture of coarse and fine filaments.

Preferably said discrete regions are formed parallel to each other and in strips that are spaced apart from each other. Thus, the product is preferred for use in a field of application when the compound web material serve as a covering layer or covering web for a diaper, sanitary napkins, incontinency products, for the entire field of hygiene, etc.

BRIEF DESCRIPTION OF THE DRAWINGS

The invention is explained in detail in the following with reference to the embodiments shown in the drawings.

FIG. 5 is a diagrammatic cross-sectional view of the second variation of the invention.

FIG. 6 is a diagrammatic cross-sectional view of an embodiment of the invention.

FIG. 7 is a diagrammatic cross-sectional view of a diaper using a compound web material as the upper covering layer.

DESCRIPTION OF PREFERRED EMBODIMENTS

Figure 1:
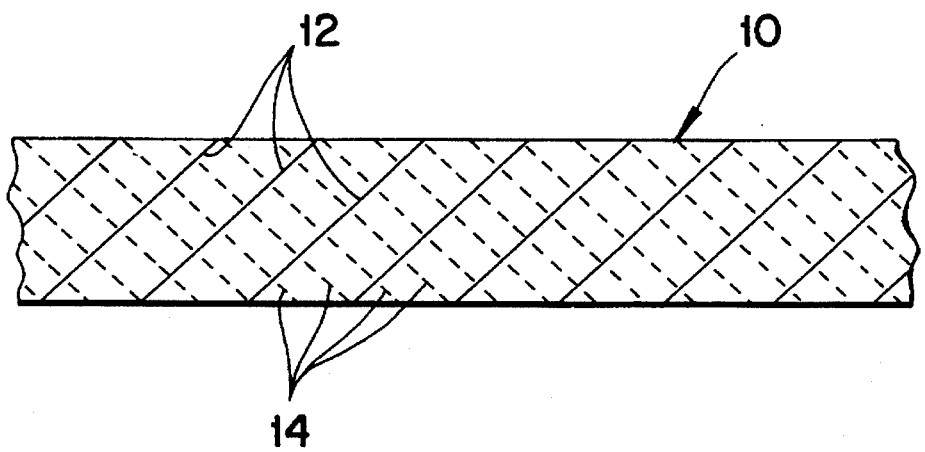
FIG. 1 is a diagrammatic cross-sectional view of the prior art compound web material.
Figure 2:
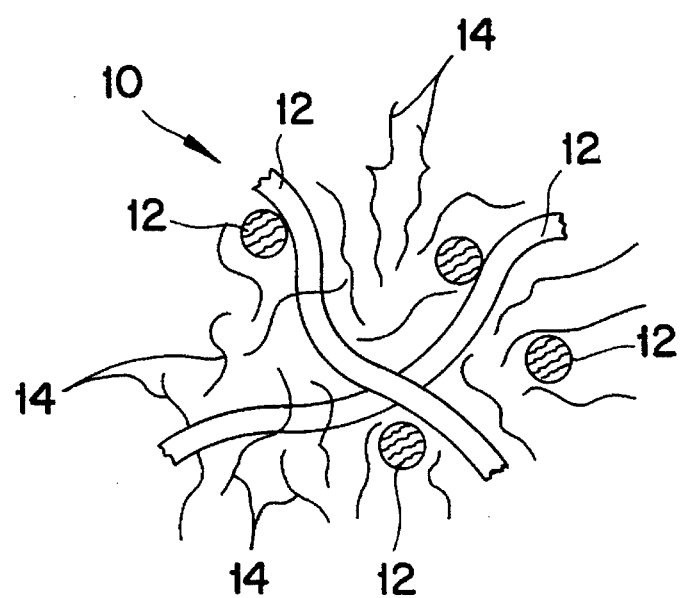
FIG. 2 is an enlarged and simplified cross-sectional view of the compound web material according to FIG. 1 wherein the substantially random alignment of the spun-bonded web components is apparent.

With the aid of FIGS. 1 and 2, a compound web material 10 according to the aforementioned German Patent Application P 39 20 066.3 is described, from which the invention starts See also the corresponding disclosure of U.S. patent application Ser. No. 07/540,221, filed on Jun. 18, 1990, where the same disclosure appears in English. The compound web material 10 consists of a mixture of coarse filaments 12 and fine microfibers 14.

To elucidate that the compound web material 10 does not have any discrete layers with a phase boundary, but rather represents a mixture, the coarse filaments 12 are denoted with solid cross-hatched lines and the fine microfibers 14 with dashed lines. Both the coarse and substantially continuous filaments 12, which exhibit molecular orientation, and the discontinuous fine microfibers 14, which exhibit substantially no molecular orientation, extend in essence over the entire thickness of the cross section of the compound web material 10 (i.e., from the upper surface to the lower surface). As an alternative to the discontinuous fine microfibers 14, which exhibit substantially no molecular orientation, fine continuous microfilaments of any molecular orientation can be used.

The compound web material 10 is made in an integrated web formation process on the same layering device of a web-forming installation (not illustrated). In so doing, the filaments 12 and the microfibers 14 are blended into a common flat area without producing any layer-like, discrete phase boundaries (i.e., discrete phase boundaries between substantially homogeneous layers of such components).

As the highly enlarged and simplified drawing in FIG. 2 illustrates, the filaments 12 and the microfibers 14 are mixed together, thus producing the mixture. In so doing, the usually short and very fine microfibers 14 largely fill the spaces between the comparably coarse filaments 12, thus already fastening with solidification somewhat the compound web material. The mixture of the compound web material 10 is formed, moreover, without the individual components, thus the filaments 12 or the microfibers 14, experiencing an intermediate hardening beforehand.

The diameter of the coarse filaments 12 is in an order of magnitude of more than 15 μm, whereas the diameter of the substantially finer microfibers 14 exhibit values of less than 10 μm.

The continuous filaments 12, which exhibit molecular orientation and which form the supporting matrix of the compound web material 10, can be a conventional spun web material (i.e., a web of spun-bonded filaments). The essentially discontinuous microfibers 14 can be manufactured in an advantageous manner, for example, according to the melt blown process. These fine microfibers are applied at a high speed on the layer of coarse filaments that was deposited immediately beforehand, so that they penetrate into the cavities of this coarse layer.

Figure 3:
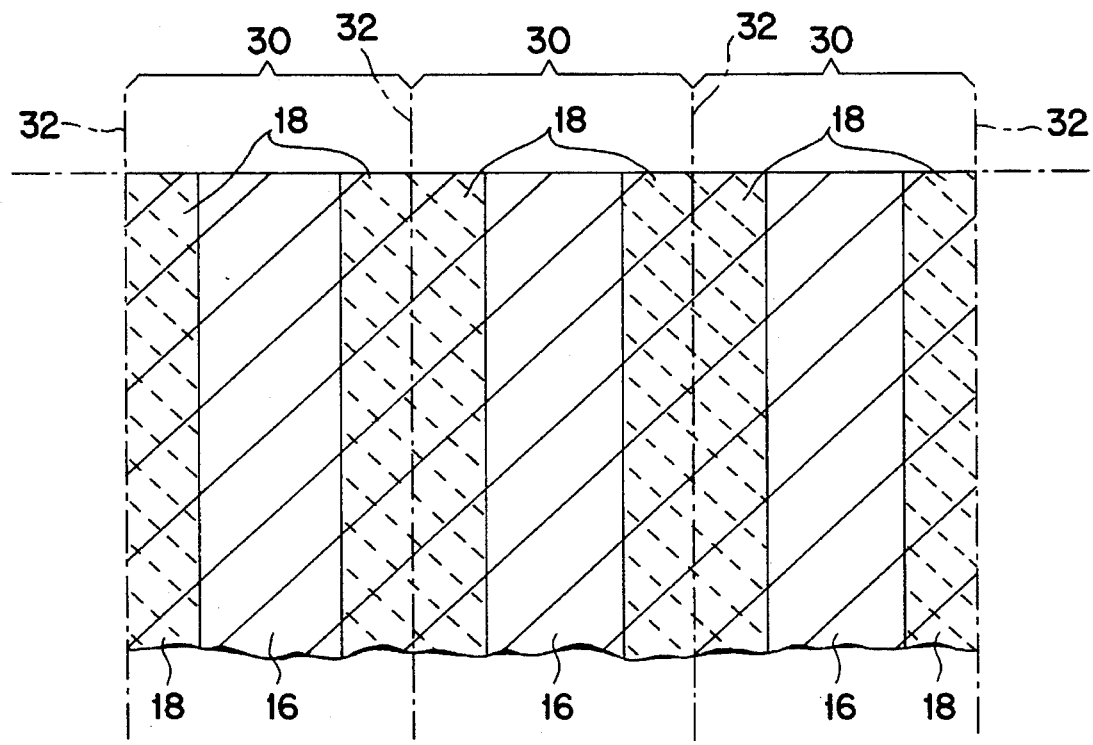
FIG. 3 is a top view of a compound web material according to the first variation of the invention.
Figure 4:
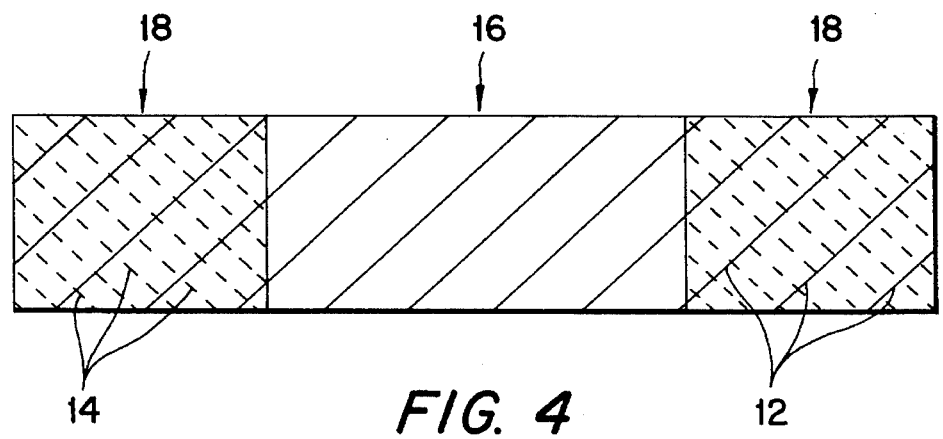
FIG. 4 is a diagrammatic cross-sectional view of the compound web material according to FIG. 3.

FIGS. 3 and 4 show a first variation of the invention. According to the top view of a web according to FIG. 3, the compound web material comprises alternating discrete strip-like regions 16 and 18. The strip-like intermediate regions 16 consist exclusively of coarse filaments, thus formed in the conventional manner as a spun web.

In contrast, the compound web material in the region of the strip-like regions 18 consists of a mixture of both components, namely coarse filaments 12 and fine microfibers 14. The dashed lines 32 indicate in FIG. 3 that diaper webs 30 can be formed from the illustrated web by slitting along lines 32. Each diaper web 30 exhibits as a covering two outer strips 18 (i.e., two preselected discrete regions 18), and between these two outer strips 18 there is the discrete intermediate region 16 formed exclusively by the spun web.

In the original state said diaper web 30 is initially hydrophobic. To utilize the diaper web 30 in a diaper, only the central strip 16 is hydrophilized, so that this central strip 16 forms a drainage region. The two outer strips 18 are hydrophobic and serve to cover the adjoining side areas of an absorptive body (not illustrated) of a diaper.

For further elucidation, FIG. 4 depicts a cross-sectional view of a diaper web 30. On both outer sides the strip-like regions 18 are apparent that are formed both by the coarse filaments and by the fine microfibers. Intermediate is the region 16 consisting exclusively of coarse filaments.

The illustrated construction of a diaper web 30 enables utilizing the highly distinctive hydrophobic properties of the fine microfibers (melt-blown) in the region of the two outer strips 18, so that for a diaper, whose absorptive body is covered with a diaper web 30, the liquid of the absorptive body is reliably prevented from rewatering the adjoining side areas. In contrast, liquid in the central drainage region—strip 16—can flow to the absorptive body. If in this region a certain rewatering could also be possible, there is still the advantage that such a rewatering is limited only to the central strip-like region 16 and does not occur in the side areas of the absorptive body, thus in the region of the outer strip 18.

This is a significant advantage over conventional diapers, where the entire area of the entire covering layer of the absorptive body is designed so as to be hydrophilic.

If a diaper web according to FIG. 4 is inserted at right angles to the direction of production of the diaper, the outer, hydrophobic strips 18 will come to lie at the front and rear ends of the diaper. When wearing the diaper, the result is less rewetting in the stomach and/or back region.

The other variation of the invention according to FIG. 5 differs from the drawing according to FIG. 4 in that the central strip 16' is not formed exclusively by coarse filaments 12, but rather also contains a specific proportion of fine microfibers 14. This proportion, however, is less compared to the proportion of fine microfibers provided in the two outer edge strips 18.

Starting from the original hydrophobic state of the entire surface, here, too, only the central region 16' is subjected to a hydrophilizing, in order to provide a drainage region. Thus, the two outer strips 18 remain hydrophobic, in order to cover the side areas of an absorptive body and to keep them dry.

The advantage of the variation according to FIG. 5 lies in the fact that the diaper web 30 is hydrophilic in the drainage region 16', but due to the small amount of free microfibers 14 small particles can be prevented from penetrating. Such small particles are, for example, in the absorptive body as a super-absorbing powder which is used in the production of the absorptive bodies.

Thus, preventing these small particles from penetrating guarantees that they cannot get through the central strip 16' to the outside.

FIG. 6 shows another embodiment of the invention that is formed in such a manner that an additional web material layer 24 is applied on one side of the diaper web 30 according to FIG. 4; said web material layer consists exclusively of coarse filaments, and thus represents a conventional spun web (this web material layer can also be applied to the diaper web according to FIG. 5).

The purpose of the additional web material layer 24 becomes clear with the aid of FIG. 7, which is a diagrammatic cross sectional view of one section of a diaper. At the top the absorptive body 26 of the diaper is covered with the compound web material according to FIG. 6, which forms thus the covering layer. In so doing, the side that is up in FIG. 6 is on the bottom here, thus in the direction of the absorptive body 26.

An outer skin 28 formed by a foil (back sheet foil) is located in a known manner on the bottom side of the absorptive body 26. This outer skin has been connected and attached to the covering layer on the side outside the absorptive body 26, so that the absorptive body 26 is entirely enclosed. The attachment is done in the usual manner by cementing the covering layer to the outer skin at the side edges of the diaper.

It has been demonstrated in everyday operations that this cementing can be deficient, if the upper covering layer contains fine microfibers. To eliminate this possible drawback, an additional web material layer 24 is inserted; said web material layer consists of a spun web and is of a coarse fiber construction. Thus, it is possible to cement the upper covering layer reliably to the outer skin 28, because the adhesive can penetrate better into the fiber structure.

In the case of sanitary napkins a web according to FIGS. 4, 5, 6 is folded in such a manner around an absorptive body that the side strips 18 containing the hydrophobic microfibers come to rest on the bottom side of the sanitary napkin. The hydrophilic central strip comprising (predominantly) the spun web represents then the moisture-permeable upper side of the sanitary napkin, whereas the hydrophobic strips form the side and back for run-out protection.

I claim:

1. An improved nonwoven covering web suitable for use in the production of absorptive products such as diapers and sanitary napkins having discrete regions possessing different drainage capabilities consisting essentially of:

(a) as a first component substantially continuous coarse spun-bonded filaments having a diameter greater than 15 μm. which exhibit molecular orientation, and (b) as a second component fine discontinuous melt-blown microfibers having a diameter less than 10 μm, wherein said first and second components of said nonwoven covering web were deposited to create a bonded integrated nonwoven structure following the simultaneous melt extrusion on the same equipment to produce in preselected discrete regions a thorough admixture of said components extending from the upper surface to the lower surface of said web wherein each component is substantially randomly aligned and is present in the absence of a discrete boundary between substantially homogeneous layers of said first and second components and wherein a discrete intermediate region was formed on the same equipment between said preselected discrete regions within said nonwoven covering web wherein the presence of said fine discontinuous melt-blown microfibers is less than the amount present in the regions where the components are in admixture or is eliminated so as to provide an area within said nonwoven covering web having an increased drainage capability when compared to said preselected discrete regions.

2. An improved nonwoven covering web according to claim 1 wherein said discrete regions and said discrete intermediate region are provided in parallel strips.

3. An improved nonwoven covering web according to claim 1 wherein said fine discontinuous melt-blown microfibers of said second component exhibit substantially no molecular orientation.

4. An improved nonwoven covering web according to claim 1 wherein no discontinuous melt-blown microfibers of said second component are present in said intermediate region so as to provide said area having an increased drainage capability.

5. An improved nonwoven covering web according to claim 1 wherein an additional web consisting solely of said coarse spun-bonded filaments of said first component is applied to one surface of said nonwoven covering web.

* * * * *